(12) United States Patent
Blackmon et al.

(10) Patent No.: US 12,011,034 B2
(45) Date of Patent: Jun. 18, 2024

(54) CAPSULES INCLUDING EMBEDDED HEATERS AND HEAT-NOT-BURN (HNB) AEROSOL-GENERATING DEVICES

(71) Applicant: Altria Client Services LLC, Richmond, VA (US)

(72) Inventors: Zack W. Blackmon, Richmond, VA (US); Eric Hawes, Midlothian, VA (US); Rangaraj S. Sundar, Midlothian, VA (US); Raymond W. Lau, Glen Allen, VA (US); Jarrett Keen, Richmond, VA (US); Yannick Hourmand, Haslingfield (GB)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 521 days.

(21) Appl. No.: 17/151,277

(22) Filed: Jan. 18, 2021

(65) Prior Publication Data

US 2022/0225667 A1 Jul. 21, 2022

(51) Int. Cl.
*A24F 40/20* (2020.01)
*A24F 40/42* (2020.01)
*A24F 40/46* (2020.01)

(52) U.S. Cl.
CPC .............. *A24F 40/20* (2020.01); *A24F 40/42* (2020.01); *A24F 40/46* (2020.01)

(58) Field of Classification Search
CPC . A24D 3/17; A24F 40/20; A24F 40/40; A24F 40/42; A24F 40/46; A24F 40/50
See application file for complete search history.

(56) References Cited

U.S. PATENT DOCUMENTS

| 855,984 A | 6/1907 | Russell |
| 1,071,389 A | 8/1913 | Blosser |
| (Continued) | | |

FOREIGN PATENT DOCUMENTS

| CN | 103945716 A | 7/2014 |
| CN | 203986136 U | 12/2014 |
| (Continued) | | |

OTHER PUBLICATIONS

Crafty Vaporizer manual (2014).
International Search Report and Written Opinion for PCT/US2021/060512 dated Apr. 21, 2022.

*Primary Examiner* — Abdullah A Riyami
*Assistant Examiner* — Thang H Nguyen
(74) *Attorney, Agent, or Firm* — Harness, Dickey & Pierce, P.L.C.

(57) ABSTRACT

A capsule for an aerosol-generating device may include a housing defining inlet openings, outlet openings, and a chamber between the inlet openings and the outlet openings. The chamber may have a longest dimension extending from at least one of the inlet openings to a corresponding one of the outlet openings. An aerosol-forming substrate may be disposed within the chamber of the housing. A heater may extend into the housing from an exterior thereof. The heater includes a first end section, an intermediate section, and a second end section. The intermediate section may be disposed within the aerosol-forming substrate in the chamber. An aerosol-generating device may include the capsule, a mouthpiece, and a device body, wherein the mouthpiece is configured to engage with the capsule, and the device body is configured to receive and retain the capsule and the mouthpiece.

18 Claims, 12 Drawing Sheets

(56) References Cited

U.S. PATENT DOCUMENTS

| | | | |
|---|---|---|---|
| 1,934,887 A | 11/1933 | Robinson | |
| 4,214,146 A | 7/1980 | Schimanski | |
| 4,564,748 A | 1/1986 | Gupton | |
| 4,947,874 A | 8/1990 | Brooks et al. | |
| 5,388,572 A | 2/1995 | Mulhauser et al. | |
| 5,388,573 A | 2/1995 | Mulhauser et al. | |
| 5,441,060 A | 8/1995 | Rose et al. | |
| 5,460,173 A | 10/1995 | Mulhauser et al. | |
| 5,593,792 A | 1/1997 | Farrier et al. | |
| 5,619,984 A | 4/1997 | Hodson et al. | |
| 5,645,050 A | 7/1997 | Zierenberg et al. | |
| 5,665,262 A | 9/1997 | Hajaligol et al. | |
| 5,823,182 A | 10/1998 | Van Oort | |
| 6,006,747 A | 12/1999 | Eisele et al. | |
| 6,065,472 A | 5/2000 | Anderson et al. | |
| 6,095,153 A | 8/2000 | Kessler et al. | |
| 6,481,437 B1 | 11/2002 | Pate | |
| 7,186,958 B1 | 3/2007 | Nelson | |
| 7,997,280 B2 | 8/2011 | Rosenthal | |
| 8,488,952 B2 | 7/2013 | Landry | |
| 8,490,627 B2 | 7/2013 | Levin et al. | |
| 8,714,150 B2 | 5/2014 | Alelov | |
| 8,910,630 B2 | 12/2014 | Todd | |
| 9,693,587 B2 | 7/2017 | Plojoux et al. | |
| 9,775,379 B2 | 10/2017 | Davidson et al. | |
| 9,943,114 B2 | 4/2018 | Batista | |
| 10,172,390 B2 | 1/2019 | Nakano et al. | |
| 10,179,215 B2 | 1/2019 | Raichman | |
| 10,219,543 B2 | 3/2019 | Gill et al. | |
| 10,247,443 B2 | 4/2019 | Flick | |
| 10,271,578 B2 | 4/2019 | John et al. | |
| 10,292,436 B2 | 5/2019 | Cirillo et al. | |
| 10,328,443 B2 | 6/2019 | Ricketts et al. | |
| 10,602,776 B2 | 3/2020 | Batista | |
| 10,820,629 B1 * | 11/2020 | O'Connell | A24F 40/10 |
| 2004/0159322 A1 | 8/2004 | Kladders et al. | |
| 2005/0063686 A1 | 3/2005 | Whittle et al. | |
| 2007/0045288 A1 | 3/2007 | Nelson | |
| 2007/0102013 A1 | 5/2007 | Adams et al. | |
| 2008/0073558 A1 | 3/2008 | Howell et al. | |
| 2009/0293888 A1 | 12/2009 | Williams et al. | |
| 2009/0293892 A1 | 12/2009 | Williams et al. | |
| 2010/0012118 A1 | 1/2010 | Storz | |
| 2010/0059070 A1 | 3/2010 | Potter et al. | |
| 2010/0078022 A1 | 4/2010 | Striebig et al. | |
| 2010/0139655 A1 | 6/2010 | Genosar et al. | |
| 2010/0313901 A1 | 12/2010 | Fernando et al. | |
| 2011/0126848 A1 | 6/2011 | Zuber et al. | |
| 2011/0192399 A1 | 8/2011 | Wilke et al. | |
| 2012/0304990 A1 | 12/2012 | Todd | |
| 2012/0325227 A1 | 12/2012 | Robinson et al. | |
| 2013/0032145 A1 | 2/2013 | Adler et al. | |
| 2013/0186392 A1 | 7/2013 | Haartsen et al. | |
| 2013/0233309 A1 | 9/2013 | Todd | |
| 2013/0233312 A1 | 9/2013 | Cohn | |
| 2013/0255702 A1 | 10/2013 | Griffith, Jr. et al. | |
| 2013/0276799 A1 | 10/2013 | Davidson et al. | |
| 2014/0041655 A1 | 2/2014 | Barron et al. | |
| 2014/0060554 A1 | 3/2014 | Collett et al. | |
| 2014/0186015 A1 | 7/2014 | Breiwa, III et al. | |
| 2014/0217197 A1 | 8/2014 | Selby et al. | |
| 2014/0238423 A1 | 8/2014 | Tucker et al. | |
| 2014/0299141 A1 | 10/2014 | Flick | |
| 2014/0321837 A1 | 10/2014 | Flick | |
| 2014/0345606 A1 | 11/2014 | Talon | |
| 2014/0366609 A1 | 12/2014 | Beck et al. | |
| 2015/0059747 A1 | 3/2015 | Von Schuckmann | |
| 2016/0021932 A1 | 1/2016 | Silverstrini et al. | |
| 2016/0057811 A1 | 2/2016 | Alarcon et al. | |
| 2016/0295922 A1 | 10/2016 | John et al. | |
| 2016/0331913 A1 * | 11/2016 | Bourque | A61M 15/0043 |
| 2016/0338410 A1 | 11/2016 | Batista et al. | |
| 2016/0345630 A1 * | 12/2016 | Mironov | A61M 11/042 |
| 2017/0055584 A1 * | 3/2017 | Blandino | A24F 40/46 |
| 2017/0071251 A1 | 3/2017 | Goch | |
| 2017/0095624 A1 * | 4/2017 | Davidson | A61M 15/005 |
| 2017/0119979 A1 | 5/2017 | Davidson et al. | |
| 2017/0143042 A1 | 5/2017 | Batista et al. | |
| 2017/0144827 A1 * | 5/2017 | Batista | A24B 15/167 |
| 2017/0164657 A1 * | 6/2017 | Batista | A24F 40/42 |
| 2017/0196262 A1 | 7/2017 | Brereton et al. | |
| 2017/0311648 A1 * | 11/2017 | Gill | A24F 40/50 |
| 2018/0007960 A1 | 1/2018 | Suzuki et al. | |
| 2018/0042302 A1 * | 2/2018 | Robinson | A61M 15/06 |
| 2018/0084831 A1 | 3/2018 | Mironov | |
| 2018/0104214 A1 | 4/2018 | Raichman | |
| 2018/0214645 A1 * | 8/2018 | Reevell | A24F 40/53 |
| 2018/0235279 A1 * | 8/2018 | Wilke | H05B 3/34 |
| 2018/0242644 A1 | 8/2018 | Bessant et al. | |
| 2018/0263286 A1 * | 9/2018 | Reevell | A24F 40/40 |
| 2018/0295885 A1 | 10/2018 | Rojo-Calderon et al. | |
| 2018/0361334 A1 | 12/2018 | Bahabri | |
| 2019/0117915 A1 | 4/2019 | Raichman | |
| 2019/0208823 A1 | 7/2019 | Raichman | |
| 2019/0224430 A1 | 7/2019 | Raichman | |
| 2020/0037669 A1 * | 2/2020 | Bowen | A24F 40/46 |
| 2020/0229509 A1 * | 7/2020 | Griscik | A24F 40/46 |
| 2020/0281269 A1 * | 9/2020 | Malgat | G05D 23/2401 |
| 2020/0390149 A1 * | 12/2020 | Hepworth | A24F 40/42 |

FOREIGN PATENT DOCUMENTS

| | | |
|---|---|---|
| CN | 104349687 A | 2/2015 |
| EP | 0525720 A1 | 2/1993 |
| EP | 1007124 A1 | 6/2000 |
| EP | 1029451 A1 | 8/2000 |
| EP | 1385595 A2 | 2/2004 |
| EP | 1504768 A1 | 2/2005 |
| KR | 101319228 | 10/2013 |
| RU | 2536115 C2 | 12/2014 |
| WO | WO-2003/037306 A2 | 5/2003 |
| WO | WO-2015/116934 A1 | 8/2015 |
| WO | WO-2016/001921 A2 | 1/2016 |
| WO | WO-2016/001922 A1 | 1/2016 |
| WO | WO-2016/001923 A2 | 1/2016 |
| WO | WO-2016/001924 A2 | 1/2016 |
| WO | WO-2016/001925 A1 | 1/2016 |
| WO | WO-2016/001926 A1 | 1/2016 |
| WO | WO-2016/005533 | 1/2016 |
| WO | WO-2016/026219 A1 | 2/2016 |
| WO | WO-2020/264362 A1 | 12/2020 |
| WO | WO-2021/262265 A1 | 12/2021 |

* cited by examiner

FIG. 5
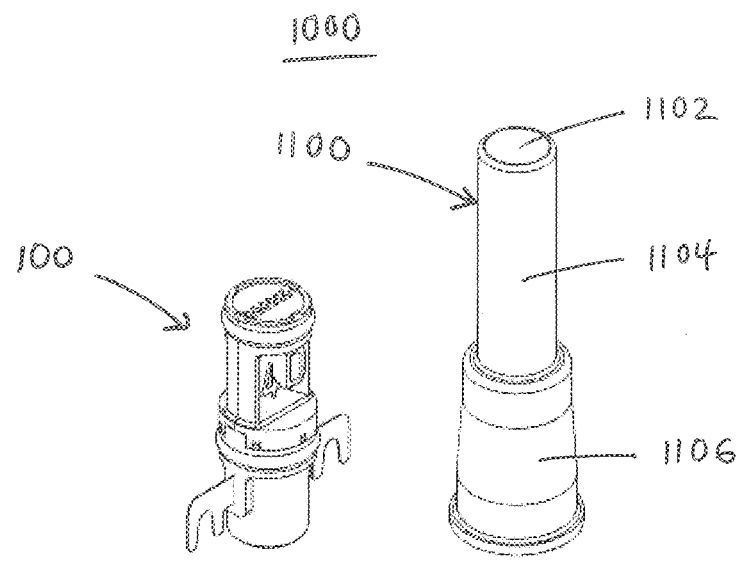
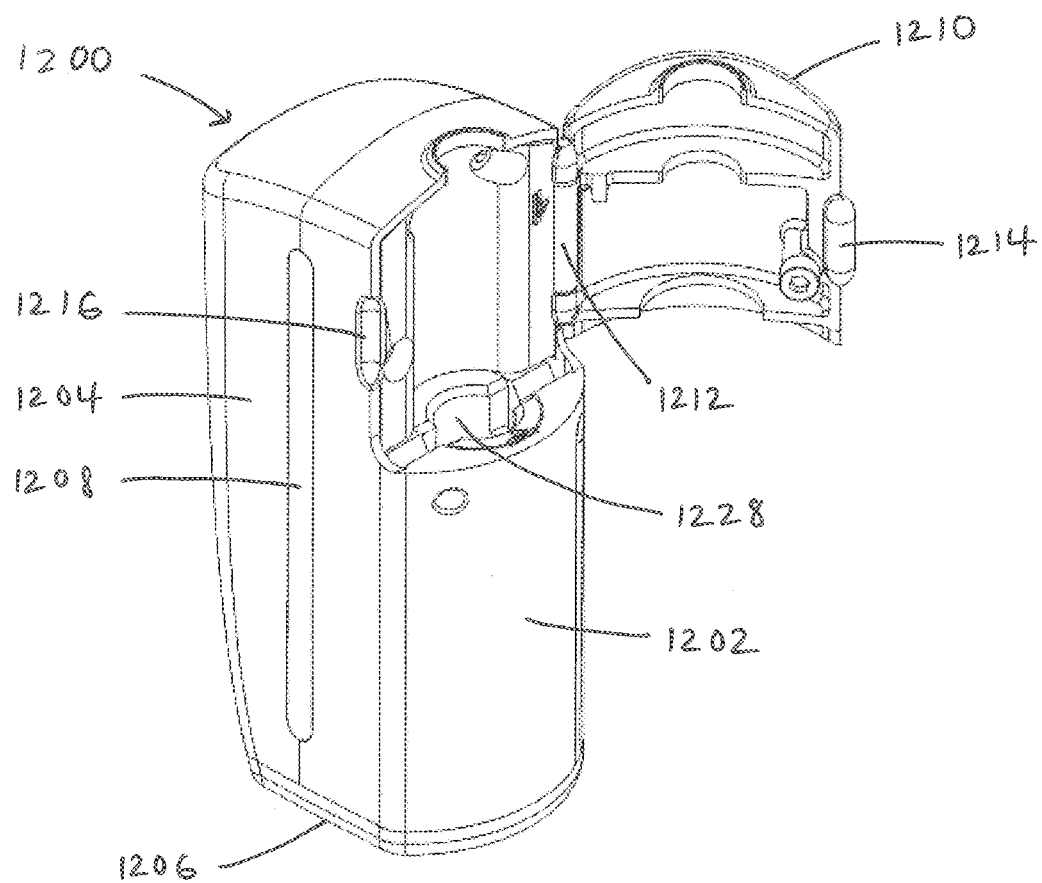

CAPSULES INCLUDING EMBEDDED HEATERS AND HEAT-NOT-BURN (HNB) AEROSOL-GENERATING DEVICES

BACKGROUND

Field

The present disclosure relates to capsules and heat-not-burn (HNB) aerosol-generating devices configured to generate an aerosol without involving a substantial pyrolysis of the aerosol-forming substrate.

Description of Related Art

Some electronic devices are configured to heat a plant material to a temperature that is sufficient to release constituents of the plant material while keeping the temperature below a combustion point of the plant material so as to avoid any substantial pyrolysis of the plant material. Such devices may be referred to as aerosol-generating devices (e.g., heat-not-burn aerosol-generating devices), and the plant material heated may be tobacco. In some instances, the plant material may be introduced directly into a heating chamber of an aerosol-generating device. In other instances, the plant material may be pre-packaged in individual containers to facilitate insertion and removal from an aerosol-generating device.

SUMMARY

At least one embodiment relates to a capsule for a heat-not-burn (HNB) aerosol-generating device. In an example embodiment, the capsule may include a housing defining inlet openings, outlet openings, and a chamber between the inlet openings and the outlet openings, the chamber having a longest dimension extending from at least one of the inlet openings to a corresponding one of the outlet openings; an aerosol-forming substrate within the chamber of the housing; and a heater extending into the housing from an exterior thereof, the heater including a first end section, an intermediate section, and a second end section, the intermediate section being disposed within the aerosol-forming substrate in the chamber.

At least one embodiment relates to a heat-not-burn (HNB) aerosol-generating device. In an example embodiment, the aerosol-generating device may include a capsule including a housing, an aerosol-forming substrate, and a heater, the housing defining inlet openings, outlet openings, and a chamber between the inlet openings and the outlet openings; a mouthpiece configured to engage with the capsule so as to be in fluidic communication with the chamber via the outlet openings; and a device body configured to receive and retain the capsule and the mouthpiece, the device body including a power source configured to supply an electric current to the heater to heat the aerosol-forming substrate.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 5 is the front perspective view of the aerosol-generating device of FIG. 4, wherein the mouthpiece and the capsule are separated from the device body.

DETAILED DESCRIPTION

Figure 1:
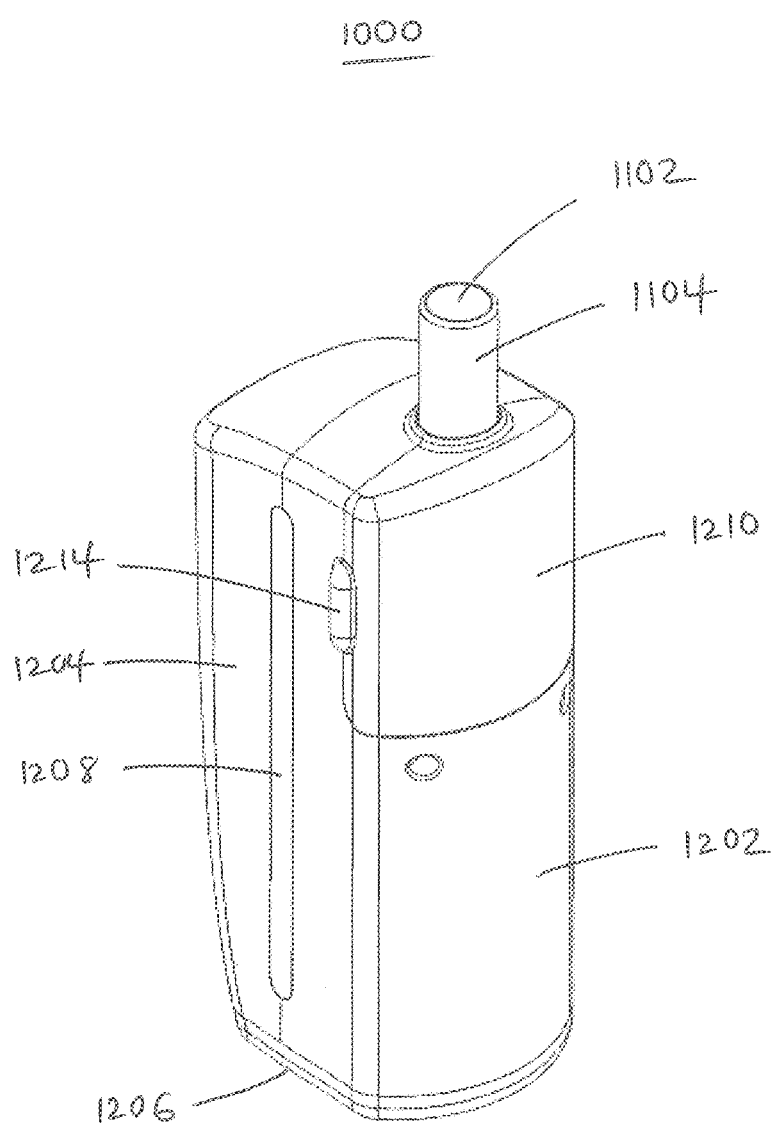
FIG. 1 is a front perspective view of an aerosol-generating device according to an example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives thereof. Like numbers refer to like elements throughout the description of the figures.

It should be understood that when an element or layer is referred to as being "on," "connected to," "coupled to," "attached to," "adjacent to," or "covering" another element or layer, it may be directly on, connected to, coupled to, attached to, adjacent to or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations or sub-combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, and/or elements, but do not preclude the presence or addition of one or more other features, integers, steps, operations, elements, and/or groups thereof.

When the terms "about" or "substantially" are used in this specification in connection with a numerical value, it is intended that the associated numerical value includes a manufacturing or operational tolerance (e.g., ±10%) around the stated numerical value. Moreover, when the terms "generally" or "substantially" are used in connection with geometric shapes, it is intended that precision of the geometric shape is not required but that latitude for the shape is within the scope of the disclosure. Furthermore, regardless of whether numerical values or shapes are modified as "about," "generally," or "substantially," it will be understood that these values and shapes should be construed as including a manufacturing or operational tolerance (e.g., ±10%) around the stated numerical values or shapes.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

The processing circuitry may be hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc.

Figure 2:
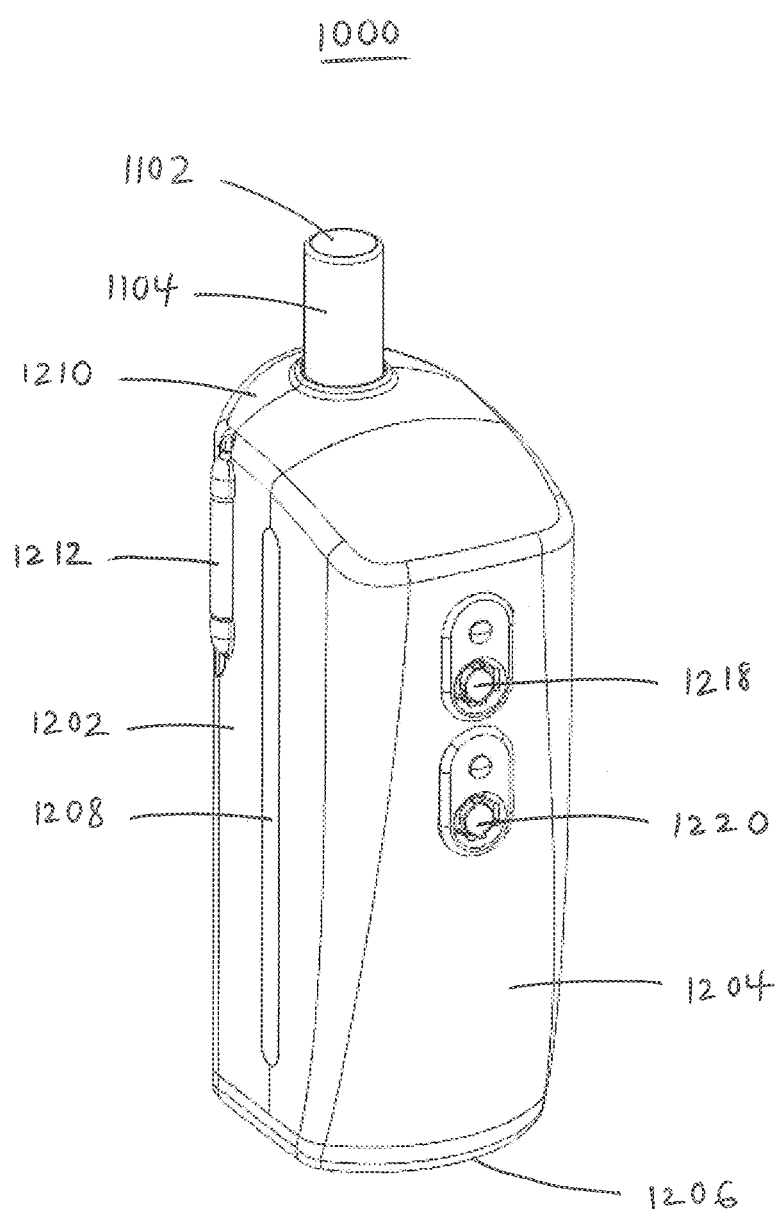
FIG. 2 is a rear perspective view of the aerosol-generating device of FIG. 1.
Figure 3:
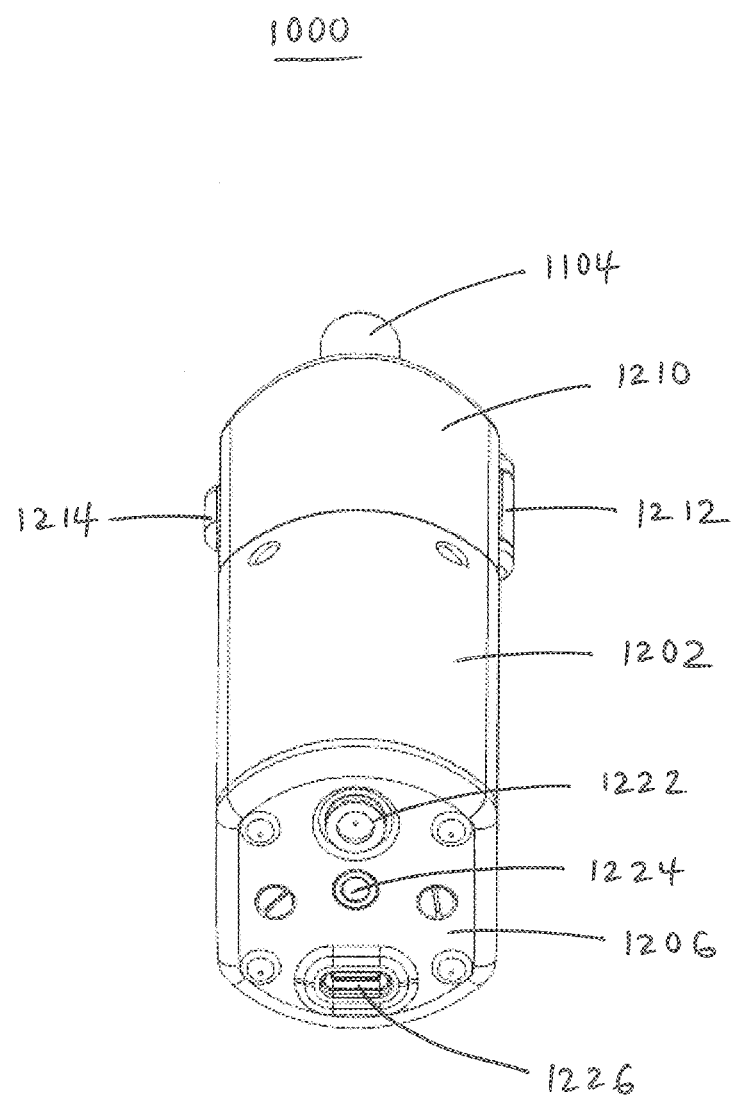
FIG. 3 is an upstream perspective view of the aerosol-generating device of FIG. 1.

FIG. 1 is a front perspective view of an aerosol-generating device according to an example embodiment. FIG. 2 is a rear perspective view of the aerosol-generating device of FIG. 1. FIG. 3 is an upstream perspective view of the aerosol-generating device of FIG. 1. Referring to FIGS. 1-3, an aerosol-generating device 1000 is configured to receive and heat an aerosol-forming substrate to produce an aerosol. The aerosol-generating device 1000 includes, inter alia, a front housing 1202, a rear housing 1204, and a bottom housing 1206 coupled to a frame 1208 (e.g., chassis). A door 1210 is also pivotally connected/attached to the front housing 1202. For instance, the door 1210 is configured to move or swing about a hinge 1212 and configured to reversibly engage/disengage with the front housing 1202 via a latch 1214 in order to transition between an open position and a closed position. The aerosol-forming substrate, which may be contained within a capsule 100 (e.g., FIG. 5), may be loaded into the aerosol-generating device 1000 via the door 1210. During an operation of the aerosol-generating device 1000, the aerosol produced may be drawn from the aerosol-generating device 1000 via the aerosol outlet 1102 defined by the mouth-end segment 1104 of the mouthpiece 1100 (e.g., FIG. 5).

As illustrated in FIG. 2, the aerosol-generating device 1000 includes a first button 1218 and a second button 1220. The first button 1218 may be a pre-heat button, and the second button 1220 may be a power button (or vice versa). Additionally, one or both of the first button 1218 and the second button 1220 may include a light-emitting diode (LED) configured to emit a visible light when the first button 1218 and/or the second button 1220 is pressed or when otherwise designated by the associated control circuitry. Where both of the first button 1218 and the second button 1220 includes an LED, the lights emitted may be of the same color or of different colors. The lights may also be of the same intensity or of different intensities. Furthermore, the lights may be configured as continuous lights or intermittent lights. For instance, the light in connection with the power button (e.g., second button 1220) may blink/flash to indicate that the power source (e.g., battery) is low and in need charging. While the aerosol-generating device 1000 is shown as having two buttons, it should be understood that more (e.g., three) or less buttons may be provided depending on the desired interface and functionalities.

The aerosol-generating device 1000 may have a cuboid-like shape which includes a front face, a rear face opposite the front face, a first side face between the front face and the rear face, a second side face opposite the first side face, a downstream end face, and an upstream end face opposite the downstream end face. As used herein, "upstream" (and, conversely, "downstream") is in relation to a flow of the aerosol, and "proximal" (and, conversely, "distal") is in relation to an adult operator of the aerosol-generating device 1000 during aerosol generation. Although the aerosol-generating device 1000 is illustrated as having a cuboid-like shape (e.g., rounded rectangular cuboid) with a polygonal cross-section, it should be understood that example embodiments are not limited thereto. For instance, in some embodiments, the aerosol-generating device 1000 may have a cylinder-like shape with a circular cross-section (e.g., for a circular cylinder) or an elliptical cross-section (e.g., for an elliptic cylinder).

As illustrated in FIG. 3, the aerosol-generating device 1000 includes an inlet insert 1222 configured to permit ambient air to enter the device body 1200 (e.g., FIG. 5). In an example embodiment, the inlet insert 1222 defines an orifice as an air inlet which is in fluidic communication with the aerosol outlet 1102. As a result, when a draw or negative pressure is applied to the aerosol outlet 1102, ambient air will be pulled into the device body 1200 via the orifice in the inlet insert 1222. The size (e.g., diameter) of the orifice in the inlet insert 1222 made be adjusted, while also taking in account other variables (e.g., capsule 100) in the flow path, to provide the desired overall resistance-to-draw (RTD). In other embodiments, the inlet insert 1222 may be omitted altogether such that the air inlet is defined by the bottom housing 1206.

The aerosol-generating device 1000 may additionally include a jack 1224 and a port 1226. In an example embodiment, the jack 1224 permits the downloading of operational information for research and development (R&D) purposes (e.g., via an RS232 cable). The port 1226 is configured to receive an electric current (e.g., via a USB/mini-USB cable) from an external power source so as to charge an internal power source within the aerosol-generating device 1000. In addition, the port 1226 may also be configured to send data to and/or receive data (e.g., via a USB/mini-USB cable) from another aerosol-generating device or other electronic device (e.g., phone, tablet, computer). Furthermore, the aerosol-generating device 1000 may be configured for wireless communication (e.g., via Bluetooth) with another electronic device, such as a phone, via an application software (app) installed on that electronic device. In such an instance, an adult operator may control or otherwise interface with the aerosol-generating device 1000 (e.g., locate the aerosol-generating device, check usage information, change operating parameters) through the app.

Figure 4:
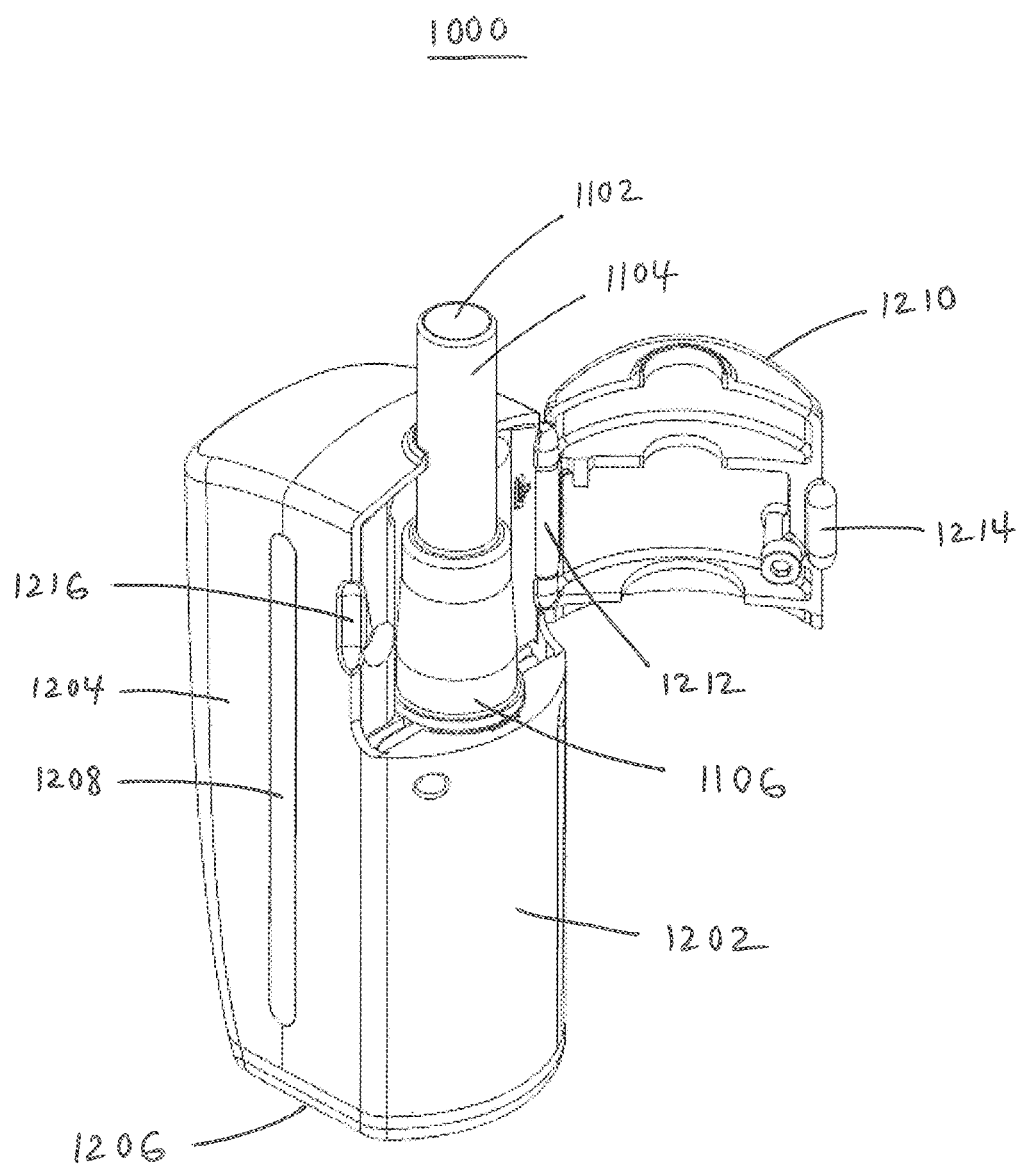
FIG. 4 is the front perspective view of the aerosol-generating device of FIG. 1, wherein the door is open.

FIG. 4 is the front perspective view of the aerosol-generating device of FIG. 1, wherein the door is open. Referring to FIG. 4, the mouthpiece 1100 includes a capsule-end segment 1106 that is visible when the door 1210 is opened and obscured/hidden from view when the door 1210 is closed. As illustrated, the capsule-end segment 1106 is larger (e.g., has a larger average diameter) than the mouth-end segment 1104. The interior of the door 1210 has contoured ridges (e.g., with semicircular indentions) configured to correspond to the curvature of the mouth-end segment 1104 and the capsule-end segment 1106 of the mouthpiece 1100. As a result, the mouthpiece 1100 may be in a relatively close fit arrangement between the front housing 1202 and the door 1210 when the door 1210 is closed. In an example embodiment, the contoured ridges on the interior of the door 1210 may be sized and positioned so as to be downstream from a larger adjacent or abutting segment of the mouthpiece 1100 when the door 1210 is closed. In this manner, the mouthpiece 1100 may be retained in a relatively secure manner so as to prevent the mouthpiece 1100 from being inadvertently detached from the device body 1200 when the door 1210 is closed.

The door 1210 is configured to swing open from a closed position (and, conversely, configured to swing closed/shut from an open position) about a hinge 1212. The hinge 1212 may be configured such that the axis of rotation for the door 1210 is parallel to the longitudinal axis of the aerosol-generating device 1000, although example embodiments are not limited thereto. The door 1210 has a latch 1214, and the front housing 1202 defines a catch 1216. The latch 1214 of the door 1210 is configured to engage with the catch 1216 of the front housing 1202 when the door 1210 is closed. The resulting engagement may be an interference fit. In another instance, the hinge 1212 may be configured (e.g., provided with the requisite friction) so as to require a continuous force to move the door 1210. In such an instance, the door 1210 will maintain its position (e.g., closed position, partially open position, fully open position) and will not freely swing open/closed based on a normal movement of the aerosol-generating device 1000. In another instance, the hinge 1212 may be spring-loaded such that the door 1210 is biased to default to a closed position. In yet another instance, the latch 1214 and the catch 1216 may be configured for a magnetic engagement. In such an instance, the latch 1214 may include a first magnet, while the catch 1216 may include a second magnet, wherein the first magnet and the second magnet are oriented to attract each other. Alternatively, one of the latch 1214 or the catch 1216 may include a magnet, while the other of the latch 1214 or the catch 1216 may include a material (e.g., ferromagnetic material) that is attracted to the magnet.

FIG. 5 is the front perspective view of the aerosol-generating device of FIG. 4, wherein the mouthpiece and the capsule are separated from the device body. Referring to FIG. 5, the aerosol-generating device 1000 includes a device body 1200 configured to receive a capsule 100 and a mouthpiece 1100. In an example embodiment, the device body 1200 defines a receptacle 1228 configured to receive the capsule 100. The receptacle 1228 may be in a form of a cylindrical socket with outwardly-extending, diametrically-opposed side slots to accommodate the electrical end sections/contacts of the capsule 100. However, it should be understood that the receptacle 1228 may be in other forms based on the shape/configuration of the capsule 100.

As noted supra, the device body 1200 includes a door 1210 configured to open to permit an insertion of the capsule 100 and the mouthpiece 1100 and configured to close to retain the capsule 100 and the mouthpiece 1100. The mouthpiece 1100 includes a mouth end (e.g., of the mouth-end segment 1104) and an opposing capsule end (e.g., of the capsule-end segment 1106). In an example embodiment, the capsule end is larger than the mouth end and configured to prevent a disengagement of the mouthpiece 1100 from the capsule 100 when the door 1210 of the device body 1200 is closed. When received/secured within the device body 1200 and ready for aerosol generation, the capsule 100 may be hidden from view while the mouth-end segment 1104 defining the aerosol outlet 1102 of the mouthpiece 1100 is visible. As illustrated in the figures, the mouth-end segment 1104 of the mouthpiece 1100 may extend from/through the downstream end face of the device body 1200. Additionally, the mouth-end segment 1104 of the mouthpiece 1100 may be closer to the front face of the device body 1200 than the rear face.

In some instances, the device body 1200 of the aerosol-generating device 1000 may optionally include a mouthpiece sensor and/or a door sensor. The mouthpiece sensor may be disposed on a rim of the receptacle 1228 (e.g., adjacent to the front face of the device body 1200). The door sensor may be disposed on a portion of the front housing 1202 adjacent to the hinge 1212 and within the swing path of the door 1210. In an example embodiment, the mouthpiece sensor and the door sensor are spring-loaded (e.g., retractable) projections configured as safety switches. For instance, the mouthpiece sensor may be retracted/depressed (e.g., activated) when the mouthpiece 1100 is fully engaged with the capsule 100 loaded within the receptacle 1228. Additionally, the door sensor may be retracted/depressed (e.g., activated) when the door 1210 is fully closed. In such instances, the control circuitry of the device body 1200 may permit an electric current to be supplied to the capsule 100 to heat the aerosol-forming substrate therein (e.g., pre-heat permitted when the first button 1218 is pressed). Conversely, the control circuitry of the device body 1200 may prevent or cease the supply of electric current when the mouthpiece sensor and/or the door sensor is not activated or deactivated (e.g., released). Thus, the heating of the aerosol-forming substrate will not be initiated if the mouthpiece 1100 is not fully inserted and/or if the door 1210 is not fully closed. Similarly, the supply of electric current to the capsule 100 will be disrupted/halted if the door 1210 is opened during the heating of the aerosol-forming substrate.

The capsule 100, which will be discussed herein in more detail, generally includes a housing defining inlet openings, outlet openings, and a chamber between the inlet openings and the outlet openings. An aerosol-forming substrate is disposed within the chamber of the housing. Additionally, a heater may extend into the housing from an exterior thereof. The housing may include a body portion and an upstream portion (e.g., base portion). The body portion of the housing includes a proximal end and a distal end. The upstream portion of the housing may be configured to engage with the distal end of the body portion.

Figure 6:
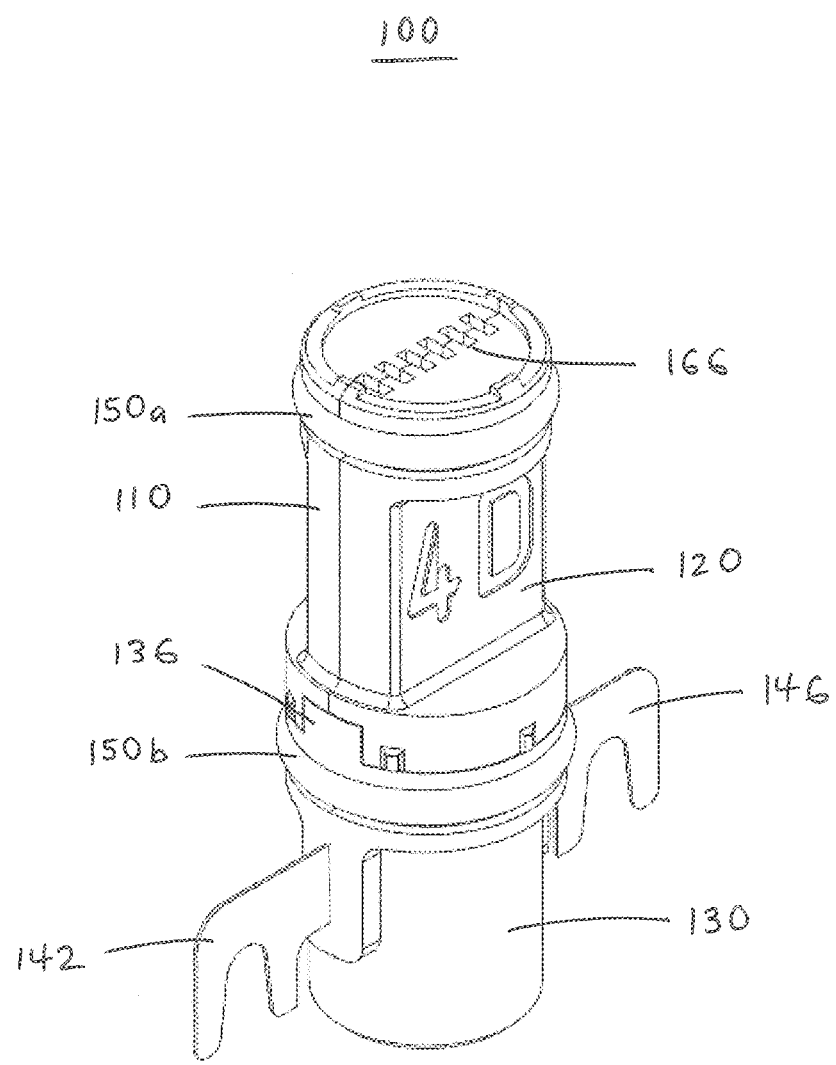
FIG. 6 is an enlarged view of the capsule in FIG. 5.
Figure 7:
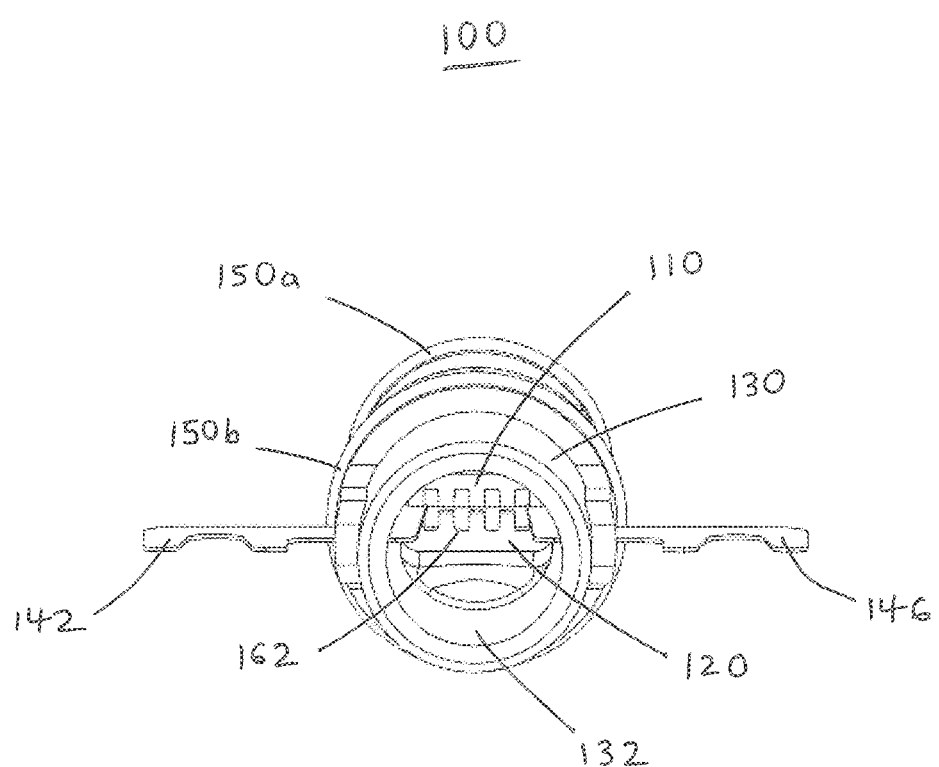
FIG. 7 is an upstream perspective view of the capsule of FIG. 6.

FIG. 6 is an enlarged view of the capsule in FIG. 5. FIG. 7 is an upstream perspective view of the capsule of FIG. 6. Referring to FIGS. 6-7, the housing of the capsule 100 may include a first cover 110, a second cover 120, and a base portion 130. Specifically, the body portion of the housing may be in the form of the first cover 110 (e.g., as a first body component) and the second cover 120 (e.g., as a second body component), while the upstream portion of the housing may be in the form of the base portion 130 (e.g., as a base component). In an example embodiment, the base portion 130 includes an engagement assembly 136, and the first cover 110 and the second cover 120 are configured to engage with each other and the base portion 130 via the engagement assembly 136. Additionally, the first cover 110 and the second cover 120 jointly define an upstream passageway 162 and a downstream passageway 166. The upstream passageway 162 may be in the form of a plurality of serially-arranged inlet openings, while the downstream passageway 166 may be in the form of a plurality of serially-arranged outlet openings, although example embodiments are not limited thereto. The base portion 130 defines a base inlet 132 (e.g., as an air channel) through which incoming air initially enters the capsule 100 before passing through the upstream passageway 162 and into the chamber within the capsule 100 where the aerosol-forming substrate is disposed. Furthermore, as will be subsequently discussed herein in more detail, the capsule 100 includes a heater 140 (e.g., FIG. 8) with a first end section 142 and a second end section 146 as external sections that extend outward from the base portion 130.

The capsule 100 may also include a first annular member 150a and a second annular member 150b. In one instance, the first annular member 150a is configured to hold together the proximal (or downstream) ends of the first cover 110 and the second cover 120. As a result, because the distal (or upstream) ends of the first cover 110 and the second cover 120 are coupled to (e.g., clamped onto) the engagement assembly 136 of the base portion 130, the first annular member 150a can help keep the first cover 110 and the second cover 120 together and, thus, prevent their inadvertent disengagement from the base portion 130. On the other hand, the second annular member 150b may be disposed on the base portion 130 so as to not physically contact the first cover 110 and the second cover 120. In an example embodiment, the first annular member 150a and the second annular member 150b are configured to help provide the desired air sealing during the operation of the aerosol-generating device 1000. Specifically, when the capsule 100 is engaged with the mouthpiece 1100, the first annular member 150a and the second annular member 150b (e.g., as resilient O-rings) may interface with the inner surface of the capsule-end segment 1106 of the mouthpiece 1100 to provide an appropriate seal. Accordingly, when a draw or negative pressure is applied to the aerosol outlet 1102 of the mouthpiece 1100, all or essentially all of the ambient air pulled into the device body 1200 may be drawn through the capsule 100 (with little or no bypass flow between outer surface of the capsule 100 and the inner surface of the mouthpiece 1100).

When the capsule 100 is loaded into the device body 1200, the first end section 142 and the second end section 146 of the heater 140 along with a majority of the base portion 130 will be seated within the receptacle 1228 (e.g., below the plane of the rim round the receptacle 1228). In an example embodiment, the receptacle 1228 of the device body 1200 may have a depth such that both the first annular member 150a and the second annular member 150b are above the rim of the receptacle 1228 when the capsule 100 is fully seated within the receptacle 1228. In such an instance, the mouthpiece 1100 will be able to interface with the first annular member 150a, the second annular member 150b, and optionally the rim around the receptacle 1228 when the mouthpiece 1100 is fully engaged with the capsule 100.

Figure 8:
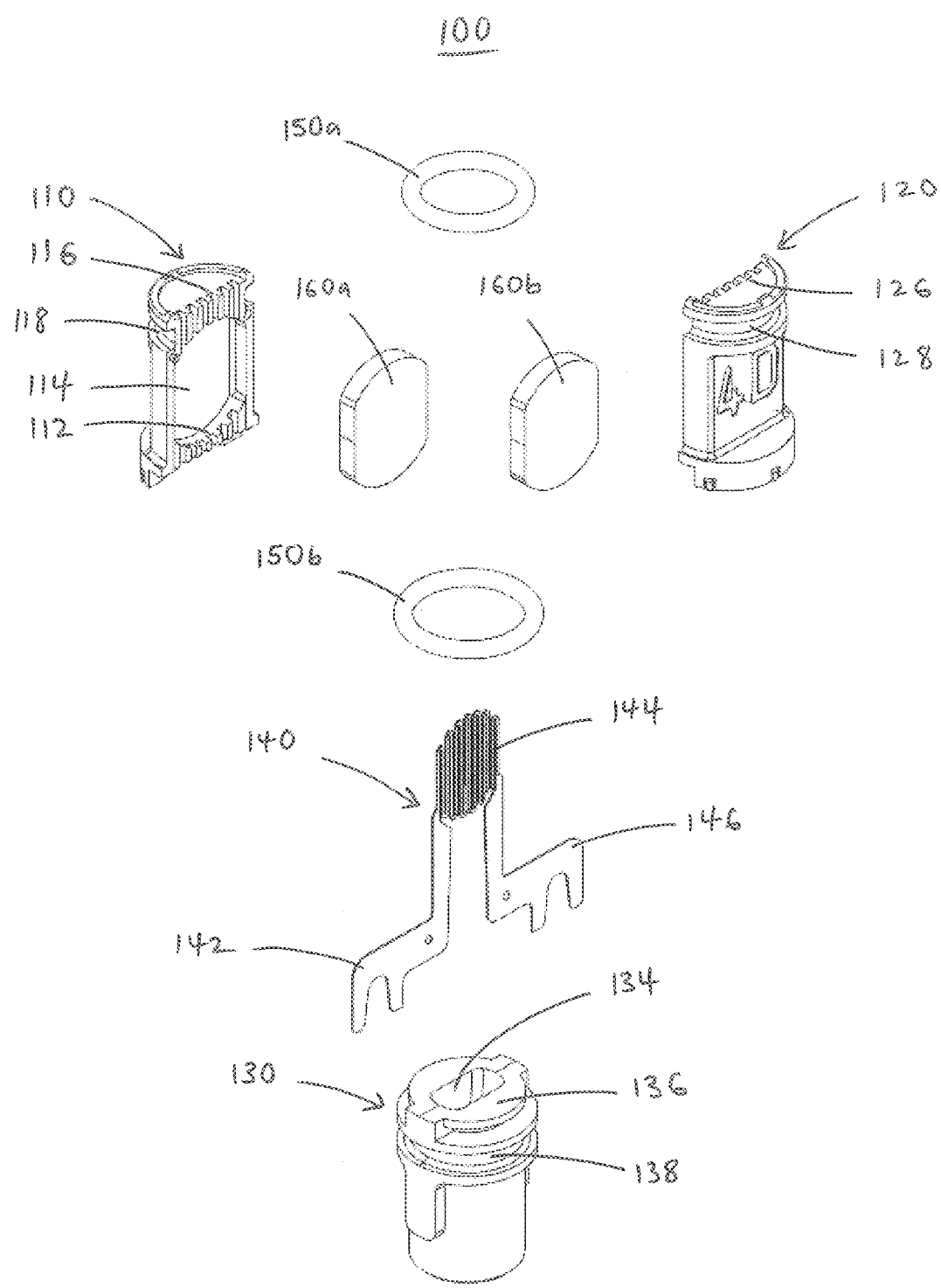
FIG. 8 is an exploded view of the capsule of FIG. 6.

FIG. 8 is an exploded view of the capsule of FIG. 6. Referring to FIG. 8, the aerosol-forming substrate contained within the capsule 100 may be in the form of a first aerosol-forming substrate 160a and a second aerosol-forming substrate 160b. In an example embodiment, the first aerosol-forming substrate 160a and the second aerosol-forming substrate 160b are housed between the first cover 110 and the second cover 120. During the operation of the aerosol-generating device 1000, the first aerosol-forming substrate 160a and the second aerosol-forming substrate 160b may be heated by a heater 140 to generate an aerosol. As will be discussed herein in more detail, the heater 140 includes a first end section 142, an intermediate section 144, and a second end section 146. Additionally, prior to the assembly of the capsule 100, the heater 140 may be mounted in the base portion 130 during a manufacturing process.

As illustrated, the first cover 110 of the capsule 100 defines a first upstream groove 112, a first recess 114, and a first downstream groove 116. The first upstream groove 112 and the first downstream groove 116 may each be in the form of a series of grooves. Similarly, the second cover 120 of the capsule 100 defines a second upstream groove, a second recess, and a second downstream groove 126. In an example embodiment, the second upstream groove, the second recess, and the second downstream groove 126 of the second cover 120 are the same as the first upstream groove 112, the first recess 114, and the first downstream groove 116, respectively, of the first cover 110. Specifically, in some instances, the first cover 110 and the second cover 120 are identical and complementary structures. In such instances, orienting the first cover 110 and the second cover 120 to face each other for engagement with the base portion 130 will result in a complementary arrangement. As a result, one part may be used interchangeably as the first cover 110 or the second cover 120, thus simplifying the method of manufacturing.

The first recess 114 of the first cover 110 and the second recess of the second cover 120 collectively form a chamber configured to accommodate the intermediate section 144 of the heater 140 when the first cover 110 and the second cover 120 are coupled with the base portion 130. The first aerosol-forming substrate 160a and the second aerosol-forming substrate 160b may also be accommodated within the chamber so as to be in thermal contact with the intermediate section 144 of the heater 140 when the capsule 100 is assembled. The chamber may have a longest dimension extending from at least one of the inlet openings (e.g., of the upstream passageway 162) to a corresponding one of the outlet openings (e.g., of the downstream passageway 166). In an example embodiment, the housing of the capsule 100 has a longitudinal axis, and the longest dimension of the chamber extends along the longitudinal axis of the housing.

The first downstream groove 116 of the first cover 110 and the second downstream groove 126 of the second cover 120 collectively form the downstream passageway 166. Similarly, the first upstream groove 112 of the first cover 110 and the second upstream groove of the second cover 120 collectively form the upstream passageway 162. The downstream passageway 166 and the upstream passageway 162 are dimensioned to be small or narrow enough to retain the first aerosol-forming substrate 160a and the second aerosol-forming substrate 160b within the chamber but yet large or wide enough to permit a passage of air and/or an aerosol therethrough when the first aerosol-forming substrate 160a and the second aerosol-forming substrate 160b are heated by the heater 140.

In one instance, each of the first aerosol-forming substrate 160a and the second aerosol-forming substrate 160b may be in a consolidated form (e.g., sheet, pallet, tablet) that is configured to maintain its shape so as to allow the first aerosol-forming substrate 160a and the second aerosol-forming substrate 160b to be placed in a unified manner within the first recess 114 of the first cover 110 and the second recess of the second cover 120, respectively. In such an instance, the first aerosol-forming substrate 160a may be disposed on one side of the intermediate section 144 of the heater 140 (e.g., side facing the first cover 110), while the second aerosol-forming substrate 160b may be disposed on the other side of the intermediate section 144 of the heater 140 (e.g., side facing the second cover 120) so as to substantially fill the first recess 114 of the first cover 110 and the second recess of the second cover 120, respectively, thereby sandwiching/embedding the intermediate section 144 of the heater 140 in between. Alternatively, one or both of the first aerosol-forming substrate 160a and the second aerosol-forming substrate 160b may be in a loose form (e.g., particles, fibers, grounds, fragments, shreds) that does not have a set shape but rather is configured to take on the shape of the first recess 114 of the first cover 110 and/or the second recess of the second cover 120 when introduced.

As noted supra, the housing of the capsule 100 may include the first cover 110, the second cover 120, and the base portion 130. When the capsule 100 is assembled, the housing may have a height (or length) of about 30 mm-40 mm (e.g., 35 mm), although example embodiments are not limited thereto. Additionally, each of the first recess 114 of the first cover 110 and the second recess of the second cover 120 may have a depth of about 1 mm-4 mm (e.g., 2 mm). In such an instance, the chamber collectively formed by the first recess 114 of the first cover 110 and the second recess of the second cover 120 may have an overall thickness of about 2 mm-8 mm (e.g., 4 mm). Along these lines, the first aerosol-forming substrate 160a and the second aerosol-forming substrate 160b, if in a consolidated form, may each have a thickness of about 1 mm-4 mm (e.g., 2 mm). As a result, the first aerosol-forming substrate 160a and the second aerosol-forming substrate 160b may be heated relatively quickly and uniformly by the intermediate section 144 of the heater 140.

As discussed herein, an aerosol-forming substrate is a material or combination of materials that may yield an aerosol. An aerosol relates to the matter generated or output by the devices disclosed, claimed, and equivalents thereof. The material may include a compound (e.g., nicotine, cannabinoid), wherein an aerosol including the compound is produced when the material is heated. The heating may be below the combustion temperature so as to produce an aerosol without involving a substantial pyrolysis of the aerosol-forming substrate or the substantial generation of combustion byproducts (if any). Thus, in an example embodiment, pyrolysis does not occur during the heating and resulting production of aerosol. In other instances, there may be some pyrolysis and combustion byproducts, but the extent may be considered relatively minor and/or merely incidental.

The aerosol-forming substrate may be a fibrous material. For instance, the fibrous material may be a botanical material. The fibrous material is configured to release a compound when heated. The compound may be a naturally occurring constituent of the fibrous material. For instance, the fibrous material may be plant material such as tobacco, and the compound released may be nicotine. The term "tobacco" includes any tobacco plant material including tobacco leaf, tobacco plug, reconstituted tobacco, compressed tobacco, shaped tobacco, or powder tobacco, and combinations thereof from one or more species of tobacco plants, such as *Nicotiana rustica* and *Nicotiana tabacum*.

In some example embodiments, the tobacco material may include material from any member of the genus *Nicotiana*. In addition, the tobacco material may include a blend of two or more different tobacco varieties. Examples of suitable types of tobacco materials that may be used include, but are not limited to, flue-cured tobacco, Burley tobacco, Dark tobacco, Maryland tobacco, Oriental tobacco, rare tobacco, specialty tobacco, blends thereof, and the like. The tobacco material may be provided in any suitable form, including, but not limited to, tobacco lamina, processed tobacco materials, such as volume expanded or puffed tobacco, processed tobacco stems, such as cut-rolled or cut-puffed stems, reconstituted tobacco materials, blends thereof, and the like. In some example embodiments, the tobacco material is in the form of a substantially dry tobacco mass. Furthermore, in some instances, the tobacco material may be mixed and/or combined with at least one of propylene glycol, glycerin, sub-combinations thereof, or combinations thereof.

The compound may also be a naturally occurring constituent of a medicinal plant that has a medically-accepted therapeutic effect. For instance, the medicinal plant may be a *Cannabis* plant, and the compound may be a cannabinoid. Cannabinoids interact with receptors in the body to produce a wide range of effects. As a result, cannabinoids have been used for a variety of medicinal purposes (e.g., treatment of pain, nausea, epilepsy, psychiatric disorders). The fibrous material may include the leaf and/or flower material from one or more species of *Cannabis* plants such as *Cannabis sativa*, *Cannabis indica*, and *Cannabis ruderalis*. In some instances, the fibrous material is a mixture of 60-80% (e.g., 70%) *Cannabis sativa* and 20-40% (e.g., 30%) *Cannabis indica*.

Examples of cannabinoids include tetrahydrocannabinolic acid (THCA), tetrahydrocannabinol (THC), cannabidiolic acid (CBDA), cannabidiol (CBD), cannabinol (CBN), cannabicyclol (CBL), cannabichromene (CBC), and cannabigerol (CBG). Tetrahydrocannabinolic acid (THCA) is a precursor of tetrahydrocannabinol (THC), while cannabidiolic acid (CBDA) is precursor of cannabidiol (CBD). Tetrahydrocannabinolic acid (THCA) and cannabidiolic acid (CBDA) may be converted to tetrahydrocannabinol (THC) and cannabidiol (CBD), respectively, via heating. In an example embodiment, heat from a heater (e.g., heater 140 shown in FIG. 8) may cause decarboxylation so as to convert the tetrahydrocannabinolic acid (THCA) in the capsule 100 to tetrahydrocannabinol (THC), and/or to convert the cannabidiolic acid (CBDA) in the capsule 100 to cannabidiol (CBD).

In instances where both tetrahydrocannabinolic acid (THCA) and tetrahydrocannabinol (THC) are present in the capsule 100, the decarboxylation and resulting conversion will cause a decrease in tetrahydrocannabinolic acid (THCA) and an increase in tetrahydrocannabinol (THC). At least 50% (e.g., at least 87%) of the tetrahydrocannabinolic acid (THCA) may be converted to tetrahydrocannabinol (THC) during the heating of the capsule 100. Similarly, in instances where both cannabidiolic acid (CBDA) and cannabidiol (CBD) are present in the capsule 100, the decarboxylation and resulting conversion will cause a decrease in cannabidiolic acid (CBDA) and an increase in cannabidiol (CBD). At least 50% (e.g., at least 87%) of the cannabidiolic acid (CBDA) may be converted to cannabidiol (CBD) during the heating of the capsule 100.

Furthermore, the compound may be or may additionally include a non-naturally occurring additive that is subsequently introduced into the fibrous material. In one instance, the fibrous material may include at least one of cotton, polyethylene, polyester, rayon, combinations thereof, or the like (e.g., in a form of a gauze). In another instance, the fibrous material may be a cellulose material (e.g., non-tobacco and/or non-*Cannabis* material). In either instance, the compound introduced may include nicotine, cannabinoids, and/or flavorants. The flavorants may be from natural sources, such as plant extracts (e.g., tobacco extract, *Cannabis* extract), and/or artificial sources. In yet another instance, when the fibrous material includes tobacco and/or *Cannabis*, the compound may be or may additionally include one or more flavorants (e.g., menthol, mint, vanilla). Thus, the compound within the aerosol-forming substrate may include naturally occurring constituents and/or non-naturally occurring additives. In this regard, it should be understood that existing levels of the naturally occurring constituents of the aerosol-forming substrate may be increased through supplementation. For example, the existing levels of nicotine in a quantity of tobacco may be increased through supplementation with an extract containing nicotine. Similarly, the existing levels of one or more cannabinoids in a quantity of *Cannabis* may be increased through supplementation with an extract containing such cannabinoids.

The first cover 110 and the second cover 120 also define a first furrow 118 and a second furrow 128, respectively. The first furrow 118 and the second furrow 128 collectively form a downstream furrow configured to accommodate the first annular member 150a. Similarly, the base portion 130 defines an upstream furrow 138 configured to accommodate the second annular member 150b. As noted supra, the base portion 130 includes an engagement assembly 136 configured to facilitate a connection with the first cover 110 and the second cover 120. The engagement assembly 136 may be an integrally formed part of the base portion 130. In an example embodiment, the base portion 130 defines a base outlet 134 in fluidic communication with the base inlet 132, and the engagement assembly 136 is in the form of a projecting rim/collar on each side of the base outlet 134. Additionally, each of the first cover 110 and the second cover 120 may define a slot configured to receive a corresponding projecting rim/collar of the engagement assembly 136. As a result, the first cover 110 and the second cover 120 (e.g., via their distal ends) may interlock with the engagement assembly 136 of the base portion 130 (while also interfacing with each other) to form the housing of the capsule 100.

A sheet material may be cut or otherwise processed (e.g., stamping, electrochemical etching, die cutting, laser cutting) to produce the heater 140. In such an instance, the heater 140 will have an integral, continuous form. The sheet material may be formed of one or more conductors configured to undergo Joule heating (which is also known as ohmic/resistive heating). Suitable conductors for the sheet material include an iron-based alloy (e.g., stainless steel, iron aluminides), a nickel-based alloy (e.g., nichrome), and/or a ceramic (e.g., ceramic coated with metal). For instance, the stainless steel may be a type known in the art as SS316L, although example embodiments are not limited thereto. The sheet material may have a thickness of about 0.10 mm-0.30 mm (e.g., 0.15 mm-0.25 mm). The heater 140 may have a resistance between 0.5 mm-2.5 Ohms (e.g., 1.0 mm-2.0 Ohms).

The heater 140 has a first end section 142, an intermediate section 144, and a second end section 146. The first end section 142 and the second end section 146 are configured to receive an electric current from a power source during an activation of the heater 140. When the heater 140 is activated (e.g., so as to undergo Joule heating), the temperature of the first aerosol-forming substrate 160a and the second aerosol-forming substrate 160b may increase, and an aerosol may be generated and drawn or otherwise released through the downstream passageway 166 of the capsule 100. The first end section 142 and the second end section 146 may each include a fork terminal to facilitate an electrical connection with the power source (e.g., via a connection bolt), although example embodiments are not limited thereto. Additionally, because the heater 140 may be produced from a sheet material, the first end section 142, the second end section 146, and the intermediate section 144 may be coplanar. Furthermore, the intermediate section 144 of the heater 140 may have a planar and winding form resembling a compressed oscillation or zigzag with a plurality of parallel segments (e.g., eight to sixteen parallel segments). In one instance, each parallel segment may have a width of about 0.28 mm-0.32 mm (e.g., 0.30 mm) and a spacing between parallel segments of about 0.30 mm-0.34 mm (e.g., 0.32 mm). However, it should be understood that other forms for the intermediate section 144 of the heater 140 are also possible (e.g., spiral form, flower-like form).

In an example embodiment, the heater 140 extends through the base portion 130. In such an instance, the terminus of each of the first end section 142 and the second end section 146 may be regarded as external segments of the heater 140 protruding from opposite sides of the base portion 130. In particular, the intermediate section 144 of the heater 140 may be on the downstream side of the base portion 130 and aligned with the base outlet 134. During manufacturing, the heater 140 may be embedded within the base portion 130 via injection molding (e.g., insert molding, overmolding). For instance, the heater 140 may be embedded such that the intermediate section 144 is evenly spaced between the pair of projecting rims/collars of the engagement assembly 136. When the capsule 100 is assembled, the intermediate section 144 of the heater 140 may be aligned between the upstream passageway 162 and the downstream passageway 166.

Although the first end section 142 and the second end section 146 of the heater 140 are shown in the drawings as projections (e.g., fins) extending from the sides of the base portion 130, it should be understood that, in some example embodiments, the first end section 142 and the second end section 146 of the heater 140 may be configured so as to constitute parts of the side surface of the capsule 100. For instance, the exposed portions of the first end section 142 and the second end section 146 of the heater 140 may be dimensioned and oriented so as to be situated/folded against the sides of the base portion 130 (e.g., while also following the underlying contour of the base portion 130). As a result, the first end section 142 and the second end section 146 may constitute a first electrical contact pad and a second electrical contact pad, respectively, as well as parts of the side surface of the capsule 100.

Figure 9:
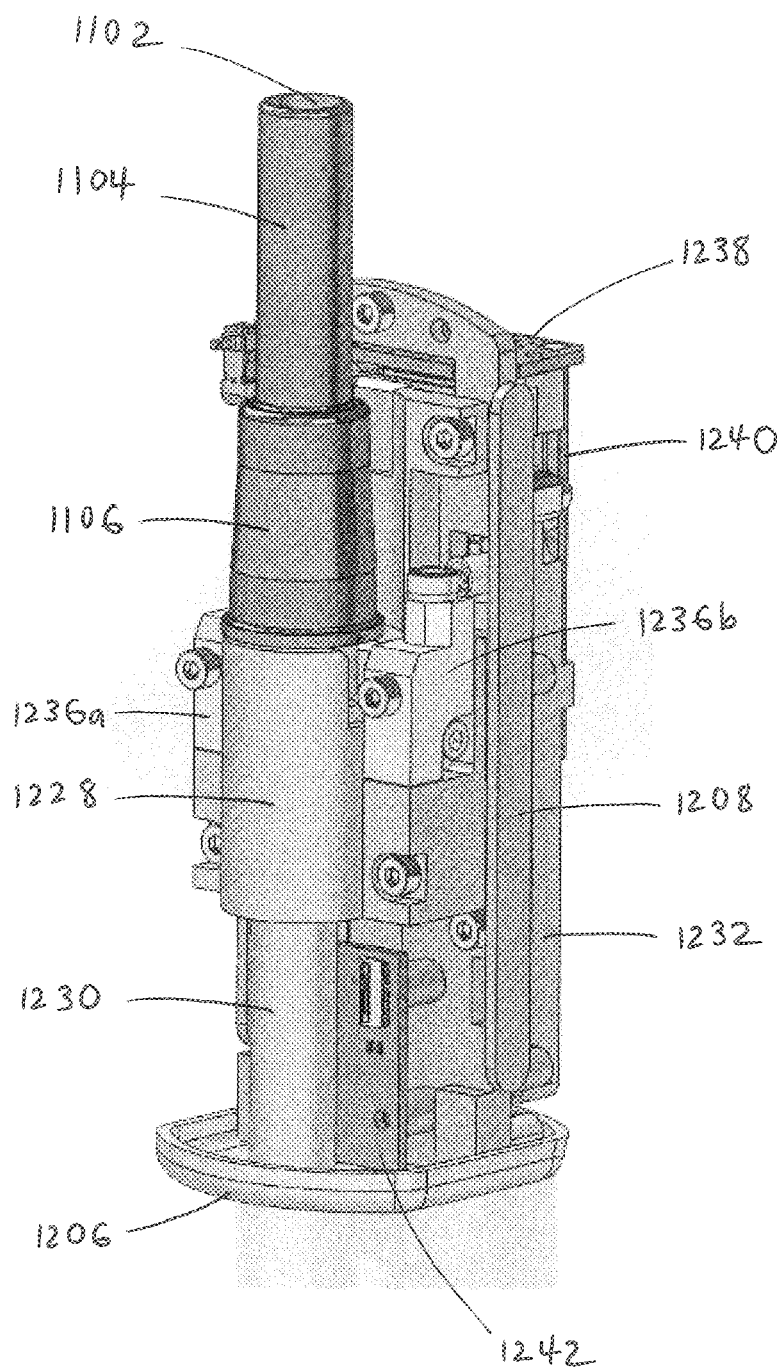
FIG. 9 is a partially-disassembled view of the aerosol-generating device of FIG. 1.
Figure 10:
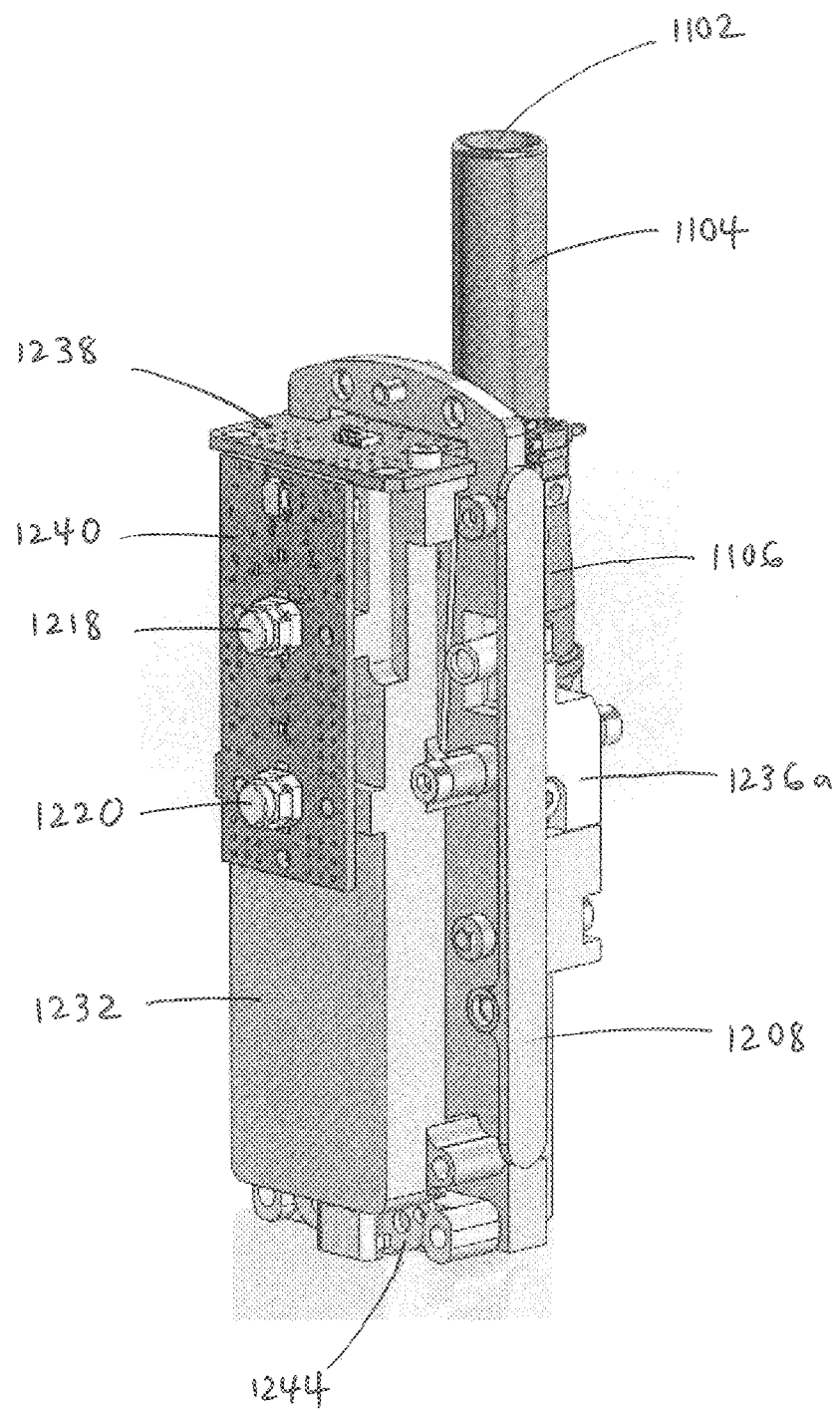
FIG. 10 is a partially-disassembled view of the aerosol-generating device of FIG. 2.

FIG. 9 is a partially-disassembled view of the aerosol-generating device of FIG. 1. FIG. 10 is a partially-disassembled view of the aerosol-generating device of FIG. 2. Referring to FIGS. 9-10, the frame 1208 (e.g., metal chassis) serves as a foundation for the internal components of the aerosol-generating device 1000, which may be attached either directly or indirectly thereto. With regard to structures/components shown in the figures and already discussed above, it should be understood that such relevant teachings are also applicable to this section and may not have been repeated in the interest of brevity. In an example embodiment, the bottom housing 1206 is secured to the upstream end of the frame 1208. Additionally, the receptacle 1228 (for receiving the capsule 100) may be mounted onto the front side of the frame 1208. Between the receptacle 1228 and the bottom housing 1206 is an inlet channel 1230 configured to direct an incoming flow of ambient air to the capsule 100 in the receptacle 1228. The inlet insert 1222 (e.g., FIG. 3), through which the incoming air may flow, may be disposed in the distal end of the inlet channel 1230. Furthermore, the receptacle 1228 and/or the inlet channel 1230 may include a flow sensor (e.g., integrated flow sensor).

A covering 1232 and a power source 1234 therein (e.g., FIG. 11) may be mounted onto the rear side of the frame 1208. To establish an electrical connection with the capsule 100 (e.g., which is in the receptacle 1228 and covered by the capsule-end segment 1106 of the mouthpiece 1100), a first power terminal block 1236a and a second power terminal block 1236b may be provided to facilitate the supply of an electric current. For instance, the first power terminal block 1236a and the second power terminal block 1236b may establish the requisite electrical connection between the power source 1234 and the capsule 100 via the first end section 142 and the second end section 146 of the heater 140. The first power terminal block 1236a and/or the second power terminal block 1236b may be formed of brass.

The aerosol-generating device 1000 may also include a plurality of printed circuit boards (PCBs) configured to facilitate its operation. In an example embodiment, a first printed circuit board 1238 (e.g., bridge PCB for power and I2C) is mounted onto the downstream end of the covering 1232 for the power source 1234. Additionally, a second printed circuit board 1240 (e.g., HMI PCB) is mounted onto the rear of the covering 1232. In another instance, a third printed circuit board 1242 (e.g., serial port PCB) is secured to the front of the frame 1208 and situated behind the inlet channel 1230. Furthermore, a fourth printed circuit board 1244 (e.g., USB-C PCB) is disposed between the rear of the frame 1208 and the covering 1232 for the power source 1234. However, it should be understood that the example embodiments herein regarding the printed circuit boards should not be interpreted as limiting since the size, shapes, and locations thereof may vary depending on the desired features of the aerosol-generating device 1000.

Figure 11:
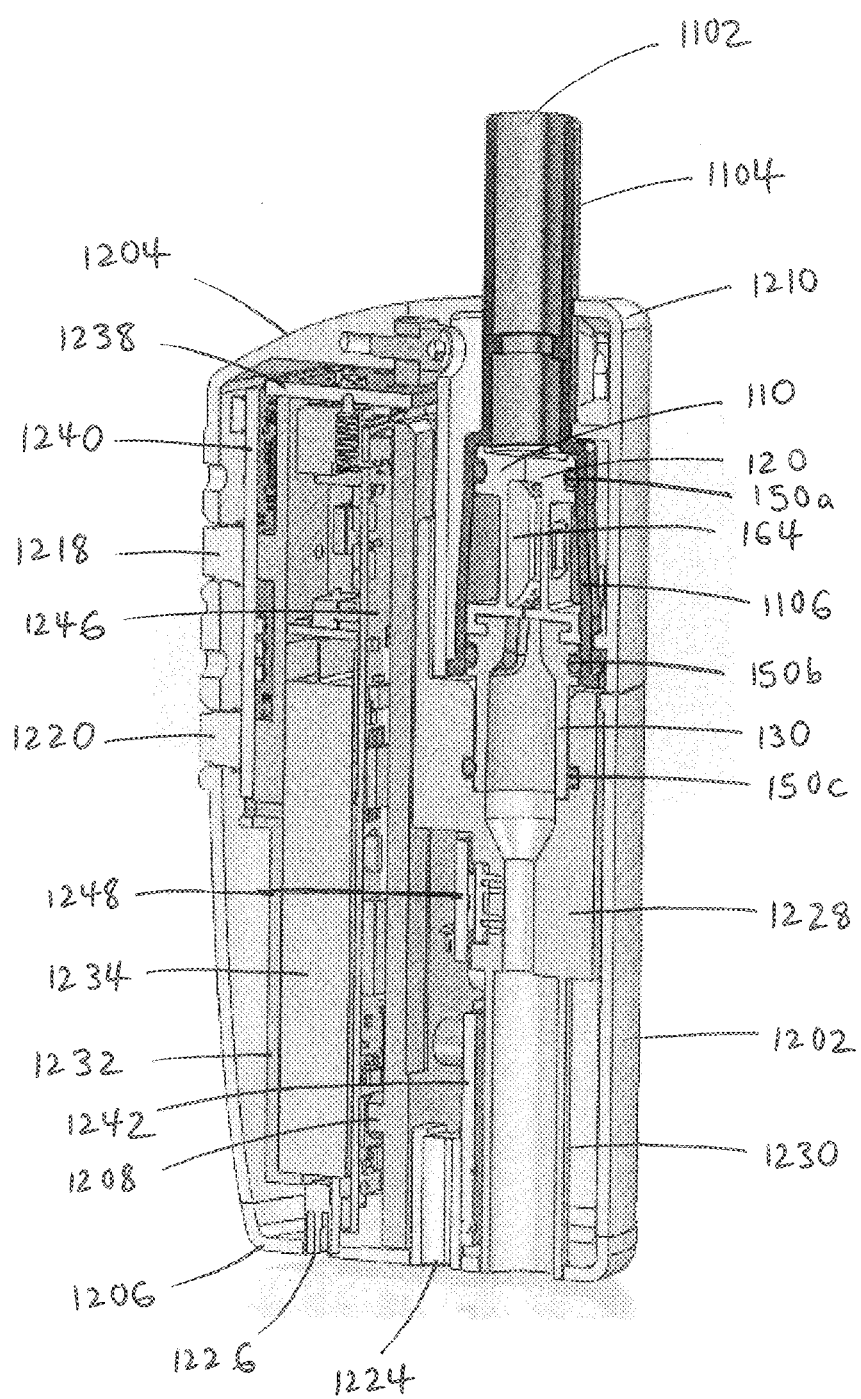
FIG. 11 is a cross-sectional view of the aerosol-generating device of FIG. 1.
Figure 12:
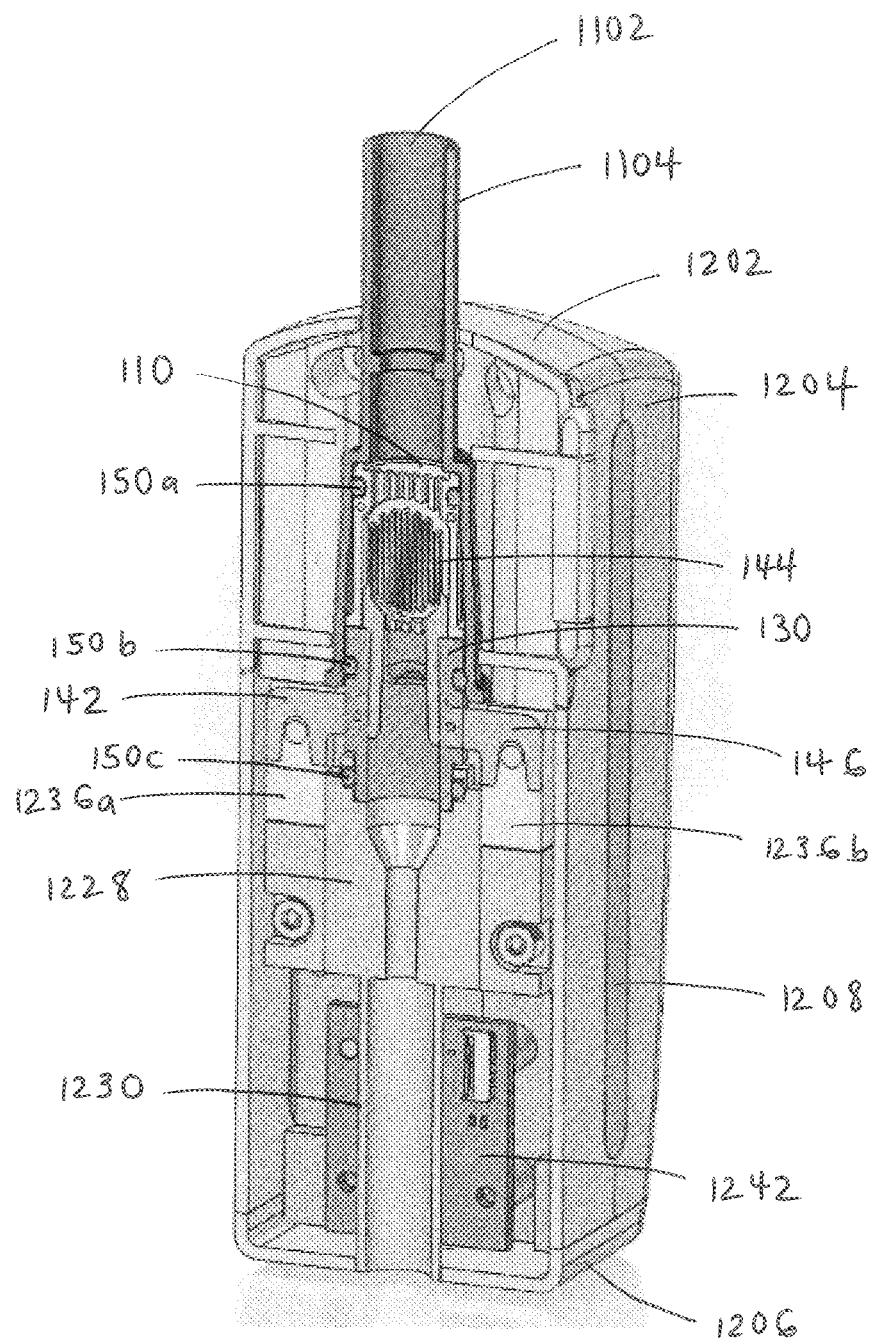
FIG. 12 is another cross-sectional view of the aerosol-generating device of FIG. 1.

FIG. 11 is a cross-sectional view of the aerosol-generating device of FIG. 1. FIG. 12 is another cross-sectional view of the aerosol-generating device of FIG. 1. With regard to structures/components shown in the figures and already discussed above, it should be understood that such relevant teachings are also applicable to this section and may not have been repeated in the interest of brevity. Referring to FIGS. 11-12, the mouth-end segment 1104 of the mouthpiece 1100 is illustrated as defining an aerosol outlet 1102 in the form of a single outlet. However, it should be understood that example embodiments are not limited thereto. For instance, the aerosol outlet 1102 may alternatively be in the form of a plurality of smaller outlets (e.g., two to six outlets). In one instance, the plurality of outlets may be in the form of four outlets. The outlets may be radially-arranged and/or outwardly-angled so as to release diverging streams of aerosol.

In an example embodiment, at least one of a filter or a flavor medium may be optionally disposed within the mouth-end segment 1104 of the mouthpiece 1100. In such an instance, a filter and/or a flavor medium will be downstream from the chamber 164 such that the aerosol generated therein passes through at least one of the filter or the flavor medium before exiting through the at least one aerosol outlet 1102. The filter may reduce or prevent particles from the aerosol-forming substrate (e.g., aerosol-forming substrate 160a and/or aerosol-forming substrate 160b) from being inadvertently drawn from the capsule 100. The filter may also help reduce the temperature of the aerosol in order to provide the desired mouth feel. The flavor medium (e.g., flavor beads) may release a flavorant when the aerosol passes therethrough so as to impart the aerosol with a desired flavor. The flavorant may be the same as described above in connection with the aerosol-forming substrate. Furthermore, the filter and/or the flavor medium may have a consolidated form or a loose form as described supra in connection with the aerosol-forming substrate.

The aerosol-generating device 1000 may also include a third annular member 150c seated within the receptacle 1228. The third annular member 150c (e.g., resilient O-ring) is configured to establish an air seal when the base portion 130 of the capsule 100 is fully inserted into the receptacle 1228. As a result, most if not all of the air drawn into the receptacle 1228 will pass through the capsule 100, and any bypass flow around the capsule 100 will be minuscule if any. In an example embodiment, the first annular member 150a, the second annular member 150b, and/or the third annular member 150c may be formed of clear silicone.

In addition to the printed circuit boards already discussed above, the aerosol-generating device 1000 may also include a fifth printed circuit board 1246 (e.g., main PCB) disposed between the frame 1208 and the power source 1234. The power source 1234 may be a 900 mAh battery (e.g., lithium-ion rechargeable battery), although example embodiments are not limited thereto. Furthermore, a sensor 1248 may be disposed upstream from the capsule 100 to enhance an operation of the aerosol-generating device 1000. For instance, the sensor 1248 may be an air flow sensor. In view of the sensor 1248 as well as the first button 1218 and the second button 1220, the operation of the aerosol-generating device 1000 may be an automatic operation (e.g., puff-activated), a manual operation (e.g., button-activated), or a combination thereof.

Upon activating the aerosol-generating device 1000, the capsule 100 within the device body 1200 may be heated to generate an aerosol. Specifically, in an example embodiment, pressing the second button 1220 will turn on the aerosol-generating device 1000. Next, pressing the first button 1218 will initiate a heating of the capsule 100 by causing the control circuitry to instruct the power source 1234 to supply an electric current to the capsule 100 via the first end section 142 and the second end section 146 of the heater 140. When the aerosol-forming substrate within the capsule 100 reaches the desired or predetermined temperature, the first button 1218 may emit a light (e.g., green light) to indicate that such a temperature (e.g., temperature for aerosol generation) has been attained. Afterwards, a draw or application of negative pressure on the aerosol outlet 1102 of the mouthpiece 1100 will pull ambient air into the device body 1200 via the inlet channel 1230, wherein the air may initially pass through an inlet insert 1222 (e.g., FIG. 3). Once inside the device body 1200, the air travels through the inlet channel 1230 to the receptacle 1228 where it is optionally detected by the sensor 1248 (e.g., for the generation of topography data). After the sensor 1248, the air continues through the receptacle 1228 and enters the capsule 100 via the base portion 130. Specifically, the air will flow through the base inlet 132 of the capsule 100 before passing through the upstream passageway 162 and into the chamber 164.

As a result of the electric current to the capsule 100, the temperature of the intermediate section 144 of the heater 140 will increase which, in turn, will cause the temperature of the aerosol-forming substrate (e.g., aerosol-forming substrate 160*a* and/or aerosol-forming substrate 160*b*) inside the chamber 164 to increase such that volatiles are released by the aerosol-forming substrate to produce an aerosol. The aerosol produced will be entrained by the air flowing through the chamber 164. In particular, the aerosol produced in the chamber 164 will pass through the downstream passageway 166 of the capsule 100 before exiting the aerosol-generating device 1000 from the aerosol outlet 1102 of the mouthpiece 1100. The control circuitry of the aerosol-generating device 1000 may include a control algorithm configured to manage the amount of energy/power (e.g., via an electric current) delivered to the heater 140 during and between draws/puffs by monitoring the temperature of the intermediate section 144 of the heater 140. Accordingly, the aerosol may be generated at/with a relatively consistent temperature.

In another example embodiment, once the aerosol-generating device 1000 is turned on, pressing the first button 1218 will initiate a pre-heating of the capsule 100 to a sub-aerosol-generating temperature (e.g., 90%-95% of the aerosol-generating temperature for the aerosol-forming substrate). Next, the activation of the aerosol-generating device 1000 to increase the sub-aerosol-generating temperature to the aerosol-generating temperature may be triggered by the detection of an airflow by the sensor 1248. During such a pre-heating stage/mode, the detection of the air flow by the sensor 1248 causes the control circuitry to instruct the power source 1234 to supply additional electric current to the capsule 100 via the first end section 142 and the second end section 146 of the heater 140 so as to attain the aerosol-generating temperature. The subsequently-generated aerosol may be drawn from the aerosol-generating device 1000 as described above.

In yet another example embodiment, the detection of an air flow by the sensor 1248 will turn on the aerosol-generating device 1000 and also initiate a heating of the capsule 100 by causing the control circuitry to instruct the power source 1234 to supply an electric current to the capsule 100 via the first end section 142 and the second end section 146 of the heater 140. Thus, in such an instance, it is not necessary to press the first button 1218 and the second button 1220 to activate the aerosol-generating device 1000. The subsequently-generated aerosol may be drawn from the aerosol-generating device 1000 as described above.

Additional details of the substrates, capsules, devices, and, methods (e.g., of heating/control) discussed herein may also be found in U.S. application Ser. No. 17/151,375, filed concurrently herewith, titled "HEAT-NOT-BURN (HNB) AEROSOL-GENERATING DEVICES INCLUDING ENERGY-BASED HEATER CONTROL, AND METHODS OF CONTROLLING A HEATER," U.S. application Ser. No. 17/161,409, filed concurrently herewith, titled "HEAT-NOT-BURN (HNB) AEROSOL-GENERATING DEVICES INCLUDING INTRA-DRAW HEATER CONTROL, AND METHODS OF CONTROLLING A HEATER," U.S. application Ser. No. 17/151,327, filed concurrently herewith, titled "HEAT-NOT-BURN (HNB) AEROSOL-GENERATING DEVICES AND CAPSULES," and U.S. application Ser. No. 17/151,336, filed concurrently herewith, titled "HEAT-NOT-BURN (HNB) AEROSOL-GENERATING DEVICES AND CAPSULES," the disclosures of each of which are incorporated herein in their entirety by reference.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. A capsule for an aerosol-generating device, comprising:
   a housing defining inlet openings, outlet openings, and a chamber between the inlet openings and the outlet openings, the chamber having a longest dimension extending from at least one of the inlet openings to a corresponding one of the outlet openings;
   an aerosol-forming substrate within the chamber of the housing; and
   a heater extending into the housing, the heater including a first end section, an intermediate section, and a second end section, the intermediate section being disposed within the aerosol-forming substrate in the chamber,
   wherein the housing has a longitudinal axis, and the longest dimension of the chamber extends along the longitudinal axis of the housing,
   wherein the housing includes a body portion and a base portion, the body portion including a proximal end and a distal end, the base portion configured to engage with the distal end of the body portion,
   wherein the body portion of the housing includes a first body component and a second body component, and
   wherein the first body component defines first upstream grooves, first downstream grooves, and a first recess in between, and the second body component defines second upstream grooves, second downstream grooves, and a second recess in between.

2. The capsule of claim 1, wherein the base portion of the housing defines an air channel in fluidic communication with the chamber via the inlet openings.

3. The capsule of claim 1, wherein the body portion of the housing defines the inlet openings, the outlet openings, and the chamber.

4. The capsule of claim 1, wherein the first upstream grooves and second upstream grooves collectively form the inlet openings of the housing, the first downstream grooves and the second downstream grooves collectively form the outlet openings of the housing, and the first recess and the second recess collectively form the chamber within the housing.

5. The capsule of claim 1, wherein the first body component and the second body component are configured to clamp onto the base portion.

6. The capsule of claim 1, wherein the first body component and the second body component are identical and complementary structures.

7. The capsule of claim 1, wherein the aerosol-forming substrate includes a first consolidated form and a second consolidated form disposed on opposite sides of the intermediate section of the heater.

8. The capsule of claim 1, wherein the aerosol-forming substrate includes a plant material.

9. The capsule of claim 8, wherein the plant material includes tobacco.

10. The capsule of claim 1, wherein the intermediate section of the heater is between the inlet openings and the outlet openings.

11. The capsule of claim 1, wherein the intermediate section of the heater has a planar and winding form.

12. The capsule of claim 1, further comprising:
at least one annular member engaged with the housing.

13. The capsule of claim 1, wherein the first body component and the second body component are identical.

14. The capsule of claim 1, wherein the first end section of the heater and the second end section of the heater protrude from opposite sides of the base portion.

15. A capsule for an aerosol-generating device, comprising:
a housing defining inlet openings, outlet openings, and a chamber between the inlet openings and the outlet openings, the chamber having a longest dimension extending from at least one of the inlet openings to a corresponding one of the outlet openings;
an aerosol-forming substrate within the chamber of the housing; and
a heater extending into the housing, the heater including a first end section, an intermediate section, and a second end section, the intermediate section being disposed within the aerosol-forming substrate in the chamber,
wherein the housing has a longitudinal axis, and the longest dimension of the chamber extends along the longitudinal axis of the housing,
wherein the housing includes a body portion and a base portion, the body portion including a proximal end and a distal end, the base portion configured to engage with the distal end of the body portion, and
wherein the heater is embedded through the housing such that segments of the first end section and the second end section are external to the housing.

16. An aerosol-generating device, comprising:
a capsule including a housing including a body portion and a base portion, the body portion including a proximal end and a distal end, the base portion configured to engage with the distal end of the body portion, an aerosol-forming substrate, and a heater, the housing defining inlet openings, outlet openings, and a chamber between the inlet openings and the outlet openings;
a mouthpiece configured to engage with the capsule so as to be in fluidic communication with the chamber via the outlet openings; and
a device body configured to receive and retain the capsule and the mouthpiece, the device body including a power source configured to supply an electric current to the heater to heat the aerosol-forming substrate,
wherein the body portion of the housing includes a first body component and a second body component, and
wherein the first body component defines first upstream grooves, first downstream grooves, and a first recess in between, and the second body component defines second upstream grooves, second downstream grooves, and a second recess in between.

17. The aerosol-generating device of claim 16, wherein the device body includes a door configured to open to permit an insertion of the capsule and the mouthpiece and configured to close to retain the capsule and the mouthpiece.

18. The aerosol-generating device of claim 17, wherein the mouthpiece includes a mouth end and an opposing capsule end, the capsule end being larger than the mouth end and configured to prevent a disengagement of the mouthpiece from the capsule when the door of the device body is closed.

* * * * *